(12) United States Patent
Drevik

(10) Patent No.: US 8,734,416 B2
(45) Date of Patent: May 27, 2014

(54) ABSORBENT ARTICLE COMPRISING A DETACHABLE STIFFENING ELEMENT

(75) Inventor: Solgun Drevik, Mölnlycke (SE)

(73) Assignee: SCA Hygiene Products AB, Gothenburg (SE)

(*) Notice: Subject to any disclaimer, the term of this patent is extended or adjusted under 35 U.S.C. 154(b) by 114 days.

(21) Appl. No.: 13/254,651

(22) PCT Filed: Mar. 6, 2009

(86) PCT No.: PCT/SE2009/050239
§ 371 (c)(1),
(2), (4) Date: Sep. 2, 2011

(87) PCT Pub. No.: WO2010/101502
PCT Pub. Date: Sep. 10, 2010

(65) Prior Publication Data
US 2012/0016331 A1 Jan. 19, 2012

(51) Int. Cl.
*A61F 13/15* (2006.01)
(52) U.S. Cl.
USPC .......... 604/385.17; 604/385.18; 604/385.201; 604/385.11; 604/385.101
(58) Field of Classification Search
USPC .......... 604/385.17, 385.18, 385.201, 385.11, 604/385.101
See application file for complete search history.

(56) References Cited

U.S. PATENT DOCUMENTS

| | | | |
|---|---|---|---|
| 6,061,881 A | 5/2000 | Takizawa et al. | |
| 6,171,425 B1 | 1/2001 | Nukina et al. | |
| 6,423,043 B1 | 7/2002 | Gustafsson | |
| 6,543,099 B1 | 4/2003 | Filion et al. | |
| 6,737,147 B2 | 5/2004 | Kennedy et al. | |
| 6,764,477 B1 | 7/2004 | Chen et al. | |
| 6,932,801 B1 | 8/2005 | Samuelsson | |
| 7,156,832 B2 | 1/2007 | Drevik et al. | |
| 2003/0125699 A1 | 7/2003 | Drevik et al. | |
| 2003/0163105 A1 | 8/2003 | Tears et al. | |

(Continued)

FOREIGN PATENT DOCUMENTS

| | | |
|---|---|---|
| CN | 1089828 A | 7/1994 |
| CN | 201070423 Y | 6/2008 |

(Continued)

OTHER PUBLICATIONS

Extended European Search Report dated May 28, 2013 issued in European patent application No. 09841226.5.

(Continued)

*Primary Examiner* — Jacqueline F. Stephens
(74) *Attorney, Agent, or Firm* — Drinker Biddle & Reath LLP

(57) ABSTRACT

An absorbent article having a longitudinal direction, a transverse direction, a front portion, a rear portion, and a crotch portion located between the front portion and the rear portion. The article includes an absorption member having an upper side intended to face a wearer during use of the article and a lower side intended to face away from the wearer during use of the article, and a stiffening element that, at least during use of the article, provides the article with a predetermined shape that enhances the fit of the article to the wearer's body. The stiffening element is secured to the lower side of the absorption member such that an outer side of the stiffening element faces away from the absorption member. The stiffening element includes a material exhibiting mechanical fastening properties at least on a part of the outer side of the stiffening element.

10 Claims, 3 Drawing Sheets

(56) References Cited

U.S. PATENT DOCUMENTS

| | | |
|---|---|---|
| 2004/0260258 A1 | 12/2004 | Hall et al. |
| 2005/0131372 A1 | 6/2005 | Wheeler et al. |
| 2008/0249496 A1 | 10/2008 | Petersen et al. |

FOREIGN PATENT DOCUMENTS

| | | |
|---|---|---|
| CN | 100404012 C | 7/2008 |
| EP | 0 788 785 | 8/1997 |
| EP | 1 395 218 | 2/2006 |
| GB | 2 151 548 | 7/1985 |
| GB | 2 399 378 | 5/2005 |
| JP | H06-502106 | 3/1994 |
| JP | 2008-011932 | 1/2008 |
| RU | 2288685 | 12/2006 |
| RU | 2351300 | 4/2009 |
| WO | WO-93/01783 | 2/1993 |
| WO | WO-93/21879 | 11/1993 |
| WO | WO-94/13239 A2 | 6/1994 |
| WO | 97/22321 | 6/1997 |
| WO | 98/17220 | 4/1998 |
| WO | 98/22061 | 5/1998 |
| WO | 98/58614 | 12/1998 |
| WO | 01/17474 | 3/2001 |
| WO | 02/087483 | 11/2002 |
| WO | WO-2005/025472 | 3/2005 |
| WO | 2006/038997 | 4/2006 |
| WO | WO-2007/064258 | 6/2007 |
| WO | 2008/093168 | 8/2008 |

OTHER PUBLICATIONS

Notice of Reasons for Rejection dated Apr. 2, 2013 issued in corresponding Japanese patent application No. 2011-552906 (with English translation thereof) (7 pages).

Chinese Office Action dated Apr. 1, 2013 issued in corresponding Chinese patent application No. 200980157896.1 (10 pages including English translation).

Chinese Office Action mailed Feb. 28, 2013 issued in corresponding Chinese Patent Application No. 20098157893.8 (15 pages including English translation).

Russian Office Action mailed Mar. 19, 2013 issued in Russian Patent Application No. 2011140483 filed Oct. 5, 2011 (7 pages including English translation).

Supplemental European Search Report issued in Application No. EP 09841223.2 on Feb. 20, 2013.

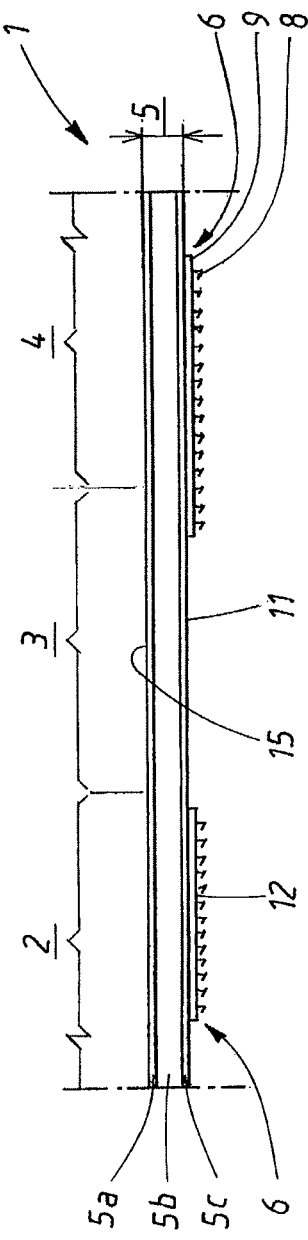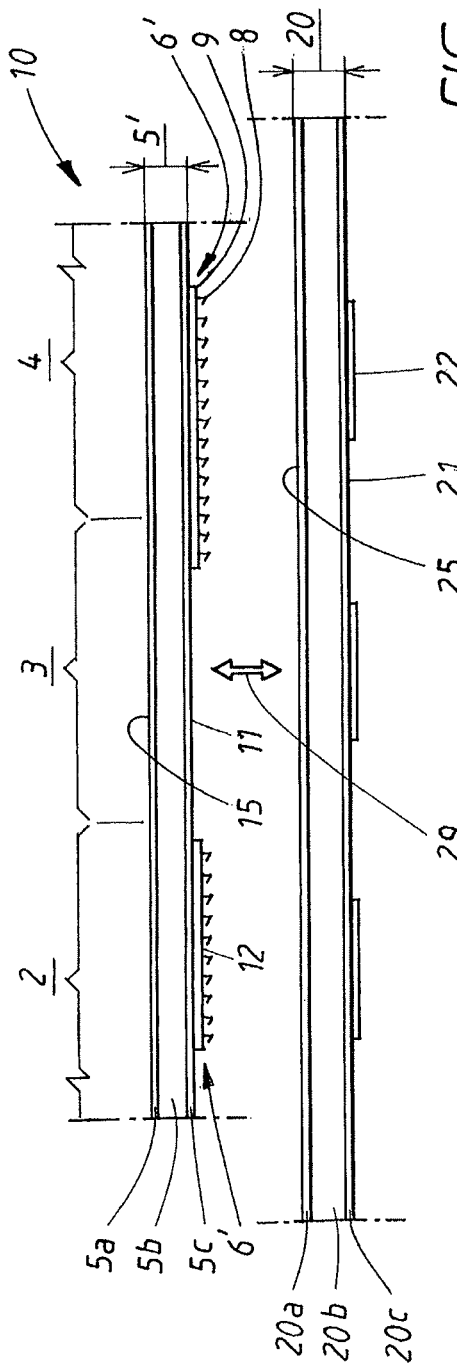

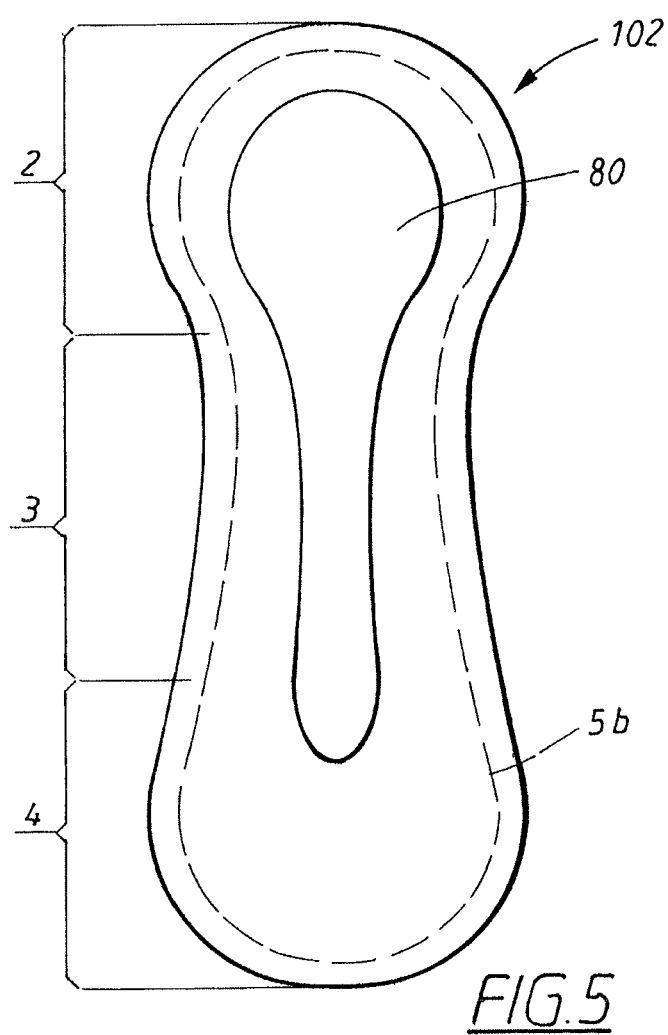

ABSORBENT ARTICLE COMPRISING A DETACHABLE STIFFENING ELEMENT

CROSS-REFERENCE TO PRIOR APPLICATION

This application is a §371 National Stage Application of PCT International Application No. PCT/SE2009/050239 filed Mar. 6, 2009, which is incorporated herein in its entirety.

FIELD OF THE INVENTION

The present disclosure relates to an absorbent article, such as a sanitary napkin, a panty liner or an incontinence protector, including an absorption member and a stiffening element that, at least during use of the article, provides the article with a certain shape that enhances the fit of the article to the wearer's body.

BACKGROUND

Absorbent articles, such as sanitary napkins, incontinence guards, panty-liners, diapers etc., are known in the art. An important function of absorbent articles is to prevent leakage of body exudates during use of the article. Generally, the article should fit well to the user and stay in place during use. This also enhances the user comfort.

With regard to at least sanitary napkins, incontinence guards and panty-liners, it is previously known to provide the article with stiff or elastic shaping elements that provide the article with a shape that improves the fitting and the ability to stay in place during use. In general, a stiff shaping element has the advantage that the shape of the article is predetermined and maintained during use. On the other hand, stiff shaping elements should be designed with particular care in order not to cause discomfort during use of the article. It is also known to provide the underside of sanitary napkins and similar absorbent articles with fastening means, such as adhesives, for attachment to the user's garments.

WO 0117474 discloses an example of an absorbent article in the form of a sanitary napkin, a panty liner or an incontinence protector, wherein the rear portion of the article includes a longitudinally extending ridge-shaped elevation forming a stiff shaping element that partially extends between the wearer's buttocks during use of the article. This provides good protection against rearward leakage.

WO 98/22061 discloses an absorbent article in the form of a sanitary napkin having stiff front and crotch portions wherein the front portion is curved and inclined upwards, towards the user, with respect to the crotch portion. Further, the article has a narrow waist in the crotch portion allowing a high stiffness without causing discomfort. The desired stiffness is achieved by e.g. including a rigid shape-retaining, spoon-shaped, plastic or metal layer inside the article. The article according to WO 98/22061 is intended to be kept securely and comfortably in position against the body of the user during use, without the need for particular attachment means.

EP 1395218 discloses an adsorbent article in the form of a sanitary towel or incontinence pad including a combined, flat stiffening and absorbent element arranged inside the article, which element gives the article in different regions a predetermined two- or three-dimensional shape (including curvature, bowl-shape and a raised part between the buttocks of the wearer) during use of the article, i.e. when the article is affected by compressive forces generated by the thighs of the wearer. In similarity to WO 98/22061, the front and crotch portions are designed to allow anchoring of the article to thigh muscle tendons, which gives the article a good fit and stability in the fitted position.

Although the known absorbent articles with stiffening elements in many cases provide for a good fit, there still remains a need to further develop this type of absorbent articles.

SUMMARY

It is desired to provide a well-fitting absorbent article, such as a sanitary napkin, that exhibits improved properties compared to conventional absorbent articles with stiff shaping elements. This can be achieved by the disclosed article.

A first aspect relates to an absorbent article, such as a sanitary napkin, a panty liner or an incontinence protector. The article has a longitudinal direction and a transverse direction, a front portion, a rear portion and a crotch portion located between the front portion and the rear portion. The article includes an absorption member having an upper side intended to face a wearer during use of the article and a lower side intended to face away from the wearer during use of the article, and a stiffening element that, at least during use of the article, provides the article with a predetermined shape that enhances the fit of the article to the wearer's body.

The stiffening element is secured to the lower side of the absorption member such that an outer side of the stiffening element faces away from the absorption member. Further, the stiffening element includes a material exhibiting mechanical fastening properties. At least a part of the outer side of the stiffening element exhibits the mechanical fastening properties.

The term absorption member as used herein refers to an item that includes an absorption body for absorption of body fluids. The absorption member may also include e.g. a liquid permeable top sheet arranged on the upper side of the absorption body and a liquid-impermeable back sheet arranged on the lower side of the absorption body.

The term mechanical fastening properties as used herein refers to mechanical fastening means such as hooks, friction adhesives, clips, friction elements and combinations thereof. The fastening means are known, and the fastening means allows for a detachable attachment. Thus, a material exhibiting mechanical fastening properties includes mechanical fastening means of the abovementioned type(s).

The absorbent article has the advantage that the stiffening element provides the article with a good body fit and at the same time allows the article to be detachably attached to the garments of a wearer or to a secondary absorption member placed below the absorption member to which the stiffening element is secured. In the latter case, the absorption member, to which the stiffening element is attached, thus forms an upper, primary absorption member arranged to be facing the wearer. Because the stiffening element provides the article with a suitable shape, it is not necessary that the (upper) absorption member contributes to the shaping of the article. Thereby it becomes possible to use a very flexible absorption member, i.e. a very flexible absorption body, which improves the comfort of the absorbent article.

The possibility of attaching the absorbent article to the garments is useful also for articles with advanced body fit, such as the one disclosed in WO 98/22061, because such articles may move in relation to the wearer during cycling or other vigorous activities. The possibility of attaching the absorbent article to a secondary absorption member placed below the one facing the wearer is useful for providing a two-part absorbent product that, for instance, may be designed to have a larger wetting area and/or a higher absorption capacity than the corresponding one-part product (i.e. the upper absorption member). Thus, the absorbent article is a convertible article that, if the user so wishes, can be converted to a two-part product at certain occasions.

Thus, in the absorbent article, the stiffening element has a multifunction: shaping and fastening. Such multifunction is generally useful for decreasing the number of components in the absorbent article which makes the manufacture more cost-effective. In the absorbent article disclosed in EP 1395218, multifunction is achieved by providing an absorbent body with a certain stiffness, i.e. stiffening (shaping) and absorbing properties are combined in the same element. However, stiffening and absorbing properties are not easily combined and such a combined element is rather costly. In contrast, the disclosed stiffening (shaping) element is a separate item in relation to the absorption element, and instead of combining stiffening and absorbing properties it combines stiffening and fastening properties which are easier to combine. For instance, improvement of the fastening properties of a piece of material does not normally lead to any corresponding impairment of the stiffening properties. Further, because the absorbing function does not have to be taken into account it is not necessary that the stiffening element has a shape in the lateral plane of the article that is adapted to this function; i.e. the stiffening element secured to the lower side of the absorption member may be e.g. rectangular to avoid or reduce wastage in the production. Because stiffening and fastening properties are easier to combine it becomes possible to manufacture the absorbent article in a more cost-effective way.

In an advantageous embodiment, the material exhibiting mechanical fastening properties also contributes significantly to the stiffness of the stiffening element. This means that the same material provides both the fastening function and, at least a great deal of, the shaping/stiffening function. This way, the structure of the stiffening element can be simplified in that the need for using particular stiffening components or layers is diminished, or even eliminated.

In a further advantageous embodiment, the material exhibiting mechanical fastening properties is a hook material having hooks protruding from the outer side of the stiffening element for fastening to a textile material. Mechanical fasteners in the form of hooks are known in the field of absorbent products to be suitable for attachment to textile materials such as undergarments or e.g. a non-woven material of a secondary absorption member. In particular embodiments, the hook material includes a hook carrier layer to which layer the hooks are secured, wherein the hook material significantly contributes to the stiffness of the stiffening member. Thereby, the hook material provides both the fastening and the stiffening/shaping functions. In a variant of this embodiment, the hook material constitutes the stiffening element. With such a design, no further materials are needed for providing the stiffening element with such functions.

In another advantageous embodiment, the material exhibiting mechanical fastening properties is a friction adhesive material. Thus, the surface of the material exhibits a stickiness that is useful for attaching the stiffening element to undergarments or e.g. a top sheet of a secondary absorption member. Also, friction adhesive materials are known. In a variant of this embodiment, the friction adhesive material constitutes the stiffening element. With such a design, no further materials are needed for providing stiffening element with such functions.

The hook material and the friction adhesive material may be combined in that certain parts of the stiffening element can include hook material and other parts can include friction adhesive material. Moreover, the absorbent article can include a plurality of stiffening elements separated from each other, which stiffening elements can include different materials. A further possibility is that the hook carrier material exhibits a stickiness.

In a further advantageous embodiment, the stiffening element exhibits a stiffness that is higher than a part of the absorbent article that surrounds the stiffening element. This has the effect that folding indications are provided along and/or around the stiffening element. These folding indications, together with e.g. the size and geometry of the stiffening element, determine which shape the article will acquire during use. In particular embodiments, the stiffening element is stiffer than the absorbent member.

In a further advantageous embodiment, the absorbent member includes an absorbent body for absorbing body fluids and a liquid-permeable top sheet arranged at the upper side of the absorption member. Thus, the top sheet faces the wearer and covers the absorbent body in a conventional way.

In a further advantageous embodiment, the absorbent member includes a liquid-impermeable back sheet arranged at the lower side of the absorption member, wherein the absorbent body is arranged between the top sheet and the back sheet. In a variant of this embodiment, the stiffening element forms at least a part of the back sheet. In other words, the stiffening element takes the place of the back sheet at some part or parts of the lower side of the absorption member. Thus, it is not necessary to make use of a conventional back sheet that completely covers the underside of the absorbent member. By using a liquid-tight stiffening element it is possible to avoid or reduce leakage in the same manner as when using a conventional back sheet.

In a further advantageous embodiment, the article includes a secondary absorption member that is detachably attachable to the stiffening element such as to be positioned below the (upper) absorbent member to which the stiffening element is secured. This way a two-part product is formed. A liquid-tight stiffening element may be used to direct body fluids to the upper absorbent member. In a variant of this embodiment, the stiffening element is arranged to allow through-flow of body fluids towards the secondary absorption member. In a further variant of this embodiment, the secondary absorption member extends further in the transversal direction, and optionally also in the longitudinal direction, than the upper absorption member. Thus, the secondary absorption member is wider, and optionally also longer, than the upper absorption member. This reduces the risk of leakage.

As used herein a permanent fixation, bond or attachment is a fixation, bond or attachment that is intended to withstand normal use and wear and that cannot be broken without destroying or damaging at least one of the items involved in the fixation. An example of a permanent fixation is the securing of the stiffening element to the lower side of the absorption member. A releasable or detachable join is a bond or attachment that can be broken without damaging or destroying the items involved.

BRIEF DESCRIPTION OF THE DRAWINGS

In the description of embodiments of the invention given below reference is made to the following figures, in which:

FIG. 1 shows, in a schematic, sectional side view, a first embodiment,

FIG. 2 shows, in a schematic, sectional side view, a second embodiment,

FIG. 5 shows the underside of an adsorbent article according to still another embodiment.

DETAILED DESCRIPTION OF PREFERRED EMBODIMENTS

Figure 3:
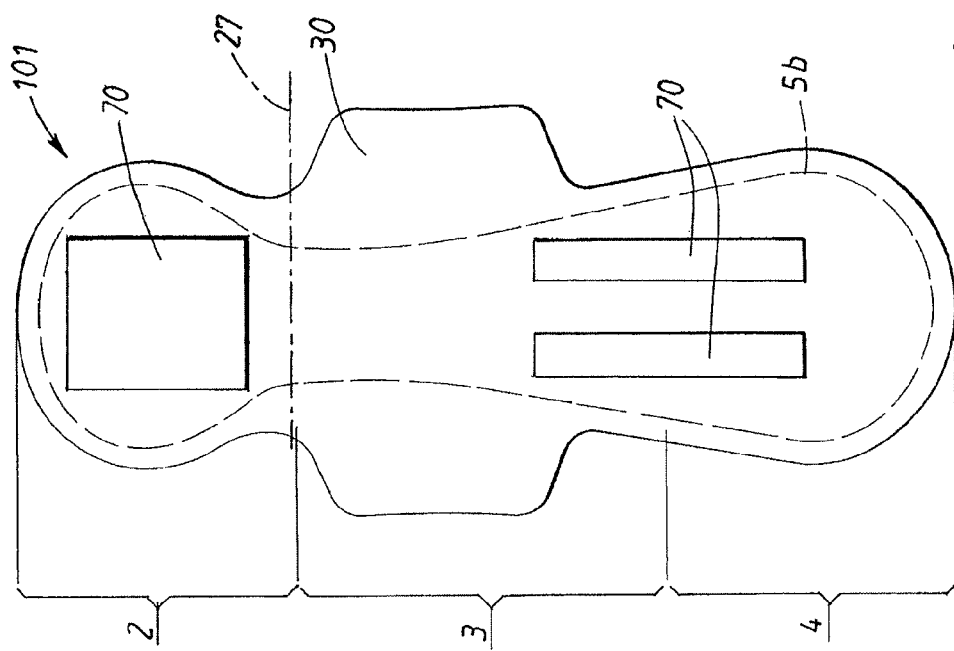
FIG. 3 shows the underside of an adsorbent article according to another a embodiment.

FIG. 1 shows, in a schematic, sectional, cut side view, a first embodiment of an absorbent article 1, in this case a sanitary napkin. The absorbent article 1 has a longitudinal direction, i.e. the left-right direction in FIG. 1, and a transverse direction, i.e. a direction perpendicular to the plane of FIG. 1. Further, the article 1 has a front portion 2, a rear portion 4 and a crotch portion 3 located between the front portion 2 and the rear portion 4. The division of the article 1 into these portions is not strict but describes, in a conventional way, the intended positioning of the article 1 in relation to a wearer. Certain components of the article 1 include an absorption member 5 and stiffening elements 6, which stiffening elements 6 in this example are two in number.

The absorption member 5 has an upper side 15 intended to face a wearer during use of the article 1 and a lower side 11 intended to face away from the wearer during use of the article 1. The absorption member 5 exemplified in FIG. 1 is in principal structured in a conventional way and includes a liquid-permeable top sheet 5a, an absorbent body 5b for absorbing body fluids, and a liquid-impermeable back sheet 5c. The top sheet 5a and the back sheet 5c are interconnected around an outer edge of the absorbent body 5b such as to form a cover around the absorbent body 5b (not shown in FIG. 1).

Suitable materials and material combinations for forming the top sheet 5a, the absorbent body 5b, and the back sheet 5c are known. Examples of suitable materials are non-woven fabrics and perforated plastic films for the top sheet 5a; cellulose fibers, absorbing foam material and super absorbents (SAP) for the absorbent body 5b; and polyethylene film and non-woven fabrics treated with hydrophobing agents for the back sheet 5c.

Each of the stiffening elements 6 extends longitudinally and transversely along the lower side 11 of the absorption member 5 such that an outer side 12 of the stiffening element 6 faces away from the absorption member 5. In this example, the stiffening element 6 is secured to the absorption member 5 by being glued to the back sheet 5c.

Because the absorption member 5 shown in FIG. 1 includes a liquid-impermeable back sheet 5c, the stiffening element 6 can be either liquid permeable or impermeable, as far as downward leakage of fluids is concerned. By using a liquid-tight stiffening element 6, and by letting the stiffening element 6 have a suitable and sufficiently large area of distribution along the lower side 11 of the absorption member 5, it is possible to exclude at least a part of the back sheet 5c and let the stiffening element 6 take the function of the back sheet 5c. It is also possible to use a less liquid resistant/more breathable back sheet in the areas surrounding the stiffening element 6.

In the example shown in FIG. 1, the stiffening element 6 is entirely made of a hook material including a hook carrier layer (hook substrate) 9 facing and being secured to the absorbent member 5, and further including a plurality of hooks 8 secured to the hook carrier layer. The hooks 8 protrude from the hook carrier layer 9, i.e. they protrude from the outer side 12 of the stiffening element 6. Hooks constitute one example of mechanical fasteners that are suitable for detachable attachment to textile materials. Thus, the stiffening element 6 in FIG. 1 is made of a material that exhibits mechanical fastening properties, wherein the outer side 12 of the stiffening element 6 exhibits such mechanical fastening properties. Other mechanical fasteners that may be used are clips or friction elements. Combinations of different types of mechanical fasteners may also be used.

The hooks 8 are suitable for interaction with the material of undergarments, which means that the absorbent article 1 according to FIG. 1 will be held in place during use by being mechanically fastened to the undergarments of the wearer.

As can be seen in FIG. 1, one of the stiffening elements 6 is positioned in the front portion 2 of the article 1 and the other extends longitudinally from the crotch portion 3 into the rear portion 4. This is similar to what is described in relation to FIG. 4. The purpose of FIGS. 1 (and 2) is, however, only to give a schematic view of the structure of the absorbent article. Different shapes of stiffening elements are described below.

FIG. 2 shows, in a schematic, sectional, cut side view and in a disassembled state, a second embodiment of an absorbent article 10, in this case a sanitary napkin. Directions and division of the article into portions are similar to what is described in relation to FIG. 1. The absorbent article 10 shown in FIG. 2 includes an upper, first absorbent member 5', a stiffening element 6', and a secondary absorption member 20. The upper absorbent member 5' has the same principal structure as the absorbent member 5 shown in FIG. 1 and the same reference numbers have therefore been used. As will be described below, there are some differences between the upper absorbent member 5' and the one shown in FIG. 1, as well as between the stiffening elements 6, 6' in FIGS. 1 and 2, respectively.

A main difference compared to the embodiment shown in FIG. 1 is that a secondary absorption member 20 is included. The secondary absorption member 20 is, via an upper side 25, detachably attachable to the stiffening elements 6', and thus to the upper absorbent member 5', such as to form a two-part product with two absorption members. In FIG. 2 the absorbent article 10 is disassembled. An arrow 29 indicates that the two absorption members 5',20 may be detachably attached to each other.

In FIG. 2, both the back sheet 5c and the stiffening element 6' are liquid permeable to allow through-flow of body fluids towards the secondary absorption member 20.

In similarity with what is described in relation to FIG. 1, the stiffening element 6' is made of a hook material including a hook carrier layer (hook substrate) 9 facing and being secured to the upper absorbent member 5' and further including a plurality of hooks 8 secured to the hook carrier layer 9. The hooks 8 protrude from the hook carrier layer and thus from the outer side 12 of the stiffening element 6'. The hooks 8 are suitable for attachment to textile materials.

When using a secondary absorption member, as exemplified in FIG. 2, it is not necessary to consider whether the hooks 8 may damage the undergarments of the wearer. In such a case it is therefore possible to make use of rougher hooks 8. Examples of such hooks are given in US 2008/0249496.

The secondary absorption member 20 has a similar structure as the absorption member 5 shown in FIG. 1, i.e. it includes a liquid-permeable top sheet 20a, an absorbent body 20b for absorbing body fluids, and a liquid-impermeable back sheet 20c. The top sheet 20a and the back sheet 20c are interconnected around an outer edge of the absorbent body 20b such as to form a cover around the absorbent body 20b (not shown in FIG. 2). In this case the top sheet 20a is made of non-woven fabrics, which allows for a good attachment to the hooks 8. A top sheet made of e.g. foam or airlaid also allows for a good attachment.

A lower side 21 of the secondary absorption member 20 is provided with fastening means 22, for instance in the form of adhesives, for attaching the absorbent article 20 to the undergarments of a user. The fastening means 22 are optional.

As can be seen in FIG. 2, the secondary absorption member 20 extends further in the longitudinal direction (i.e. sideways in FIG. 2) than does the primary, upper absorption member 5'. The secondary absorption member 20 also extends further in the transversal direction than does the primary, upper absorption member 5'. Accordingly, the secondary absorption member 20 surrounds the primary, upper absorption member 5' as seen from above, i.e. the secondary absorption member 20 exhibits a larger area as seen in a direction towards a user of the absorbent article 20 than does the primary, upper absorption member 5'. In short, in the example shown, the secondary absorption member 20 is both longer and wider than the upper absorption member 5'. This is useful for increasing the leakage protection.

With regard to FIG. 2 it should be noted that it is not necessary that the back sheet 5c and the stiffening element 6 are liquid permeable to allow body fluids to be transferred to the secondary absorption member 20. If either or both of the back sheet 5c and the stiffening element 6' are liquid impermeable, body fluids may flow transversely (and longitudinally) and pass an outer edge of either or both of these components and then reach the secondary absorption member 20. At least if the back sheet 5c is liquid impermeable it is of particular importance that the secondary absorption member 20 is wider, and optionally also longer, than the primary, upper absorption member 5'. If the stiffening element 6' has a large area of distribution, it may be equally important that the secondary absorption member 20 is larger. However, the stiffening element 6' may be arranged in the form of narrow strips or bars with openings in-between, or be provided with openings, in order to allow liquid to pass through without requiring the structuring material to be liquid permeable.

Suitable hook materials for the embodiments shown in FIGS. 1 and 2 are available as KHK0002 or CHK 00752 from 3M Company. These materials have a suitable stiffness for giving the article 1,10 a good shape during use and provides for a good attachment.

The hooks 8 can, of course, be chosen such as to be adapted to the intended use. For instance, the hooks 8 can be adapted to interact particularly well with a certain type of garment textile material or with a certain type of upper side 25 of the secondary absorption member 20.

As an alternative to the hook material described above, the stiffening element 6,6' can, at least partly, be made of a friction adhesive material, i.e. of a material that exhibits a stickiness that can be used to mechanically fasten the stiffening element 6, 6' to e.g. the undergarments of the wearer or to the secondary absorption member 20. In such a case, the top sheet 20a of the secondary absorption member 20 can be made of e.g. a nonwoven material or a perforated plastic film which allows for a good attachment to the friction adhesive material.

Friction adhesive materials, which also are referred to as friction materials, should not be confused with conventional fastening adhesives. A general difference between these materials is that the pressure sensitive adhesive of conventional fastening material does provide reasonable tack, peel and shear after a bond has been initiated by putting pressure onto the system. Different to such a behavior, a friction adhesive material will mainly provide shear. This shear or friction is proportional to the force used to press the friction material onto a second surface. After release of the pressure the system will show basically no remaining tack, peel or friction.

An example of a suitable friction adhesive material is 5401 Traction Tape available from 3M Company.

Hook material and friction adhesive material may be combined in the absorbent article 1,10 in that some parts of the stiffening element 6,6' (or some of the stiffening elements if a plurality is present) includes hook material and some includes friction adhesive material. It is also possible to use a material that has both properties, for instance a hook material that exhibits a stickiness.

The stiffening element is sufficiently stiff for, as far as possible, preventing the absorbent article from being compressed or otherwise deformed in an uncontrolled manner during use of the article.

The stiffening element 6 should exhibit a stiffness that is higher than the material of the absorbent article 1,10 that surrounds the stiffening element. In relation to the embodiments described here, this means that the stiffening element 6,6' should be stiffer than the (upper) absorbent member 5,5'. That the stiffness of the stiffening element 6,6' is higher than its surroundings has the effect that folding indications are provided along and/or around the stiffening element 6,6'. These folding indications, together with e.g. the size and geometry of the stiffening element 6,6', determine which shape the article 1,10 will acquire during use.

In particular embodiments, the stiffening element 6,6' exhibits a stiffness in a dry state in the order of 1-15 N as measured according to ASTM D 4032-82.

The stiffening elements can have a variety of shapes and positions depending on the shape desired. Various advantageous shapes of absorbent articles are known. In any case, the stiffening element(s) is/are arranged to, at least during use of the article, provide the article with a certain, predetermined shape that enhances the fit of the article to the wearer's body. A stiffening element may have a flat form before use but take a three-dimensional shape upon use of the article, i.e. when the article is affected by compressive forces generated by the thighs of the wearer. Alternatively, a stiffening element may have a three-dimensional shape already before use of the article.

In particular embodiments, the stiffening element(s) 6,6' is/are arranged such as to, at least during use of the article, provide the article with one or several of the following shapes:

A width H at a transition 27 (see FIG. 3) between the crotch portion 3 and the front portion 2 that is less than the width at the front portion 2. This allows anchoring of the article to/between the thigh muscle tendons of the user and prevents the article from moving backwards during use. In particular embodiments, the width H is in the range 15-45 mm.

A three-dimensional bowl-like shape in an area in the front portion 2. This enhances the body fit.

A ridge-shaped elevation that partially extends between the wearer's buttocks during use of the article. This prevents rearward leakage.

A raised portion (hump) intended to make contact with the genitals of the wearer during use of the article. This provides for better absorption of bodily fluids.

Figure 4:
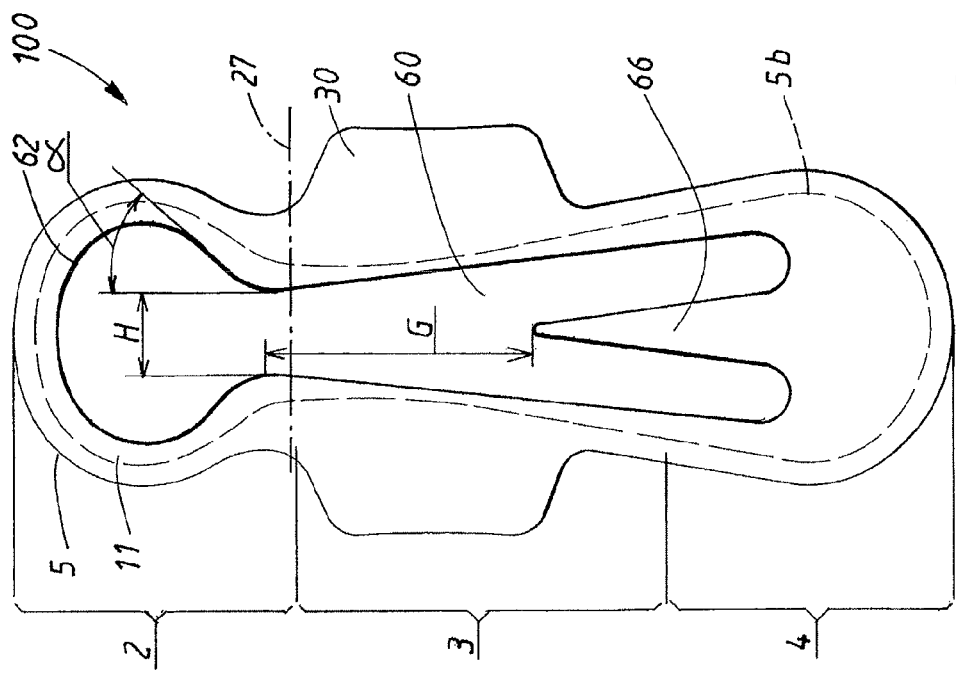
FIG. 4 shows the underside of an adsorbent article according to yet another embodiment.

FIGS. 3-5 show absorbent articles as seen from below with the main purpose of showing examples of alternative stiffening element geometries. Thus, the lower side 11 of the (upper) absorption member and the outer side 12 of the stiffening element face upwards in these figures. Any secondary absorption members are not shown. The position of the absorbent body 5b is indicated with a dashed line.

FIG. 3 shows an absorbent article 100 with a first example of a suitable shape of a stiffening element 60. In this example, the stiffening element 60 is flat and has a shape similar to what is shown in EP 1395218. A peripheral edge of the stiffening element 60 is indicated by the reference number 62. The part of the lower side 11 of the absorption member 5 that extends outside of the peripheral edge 62 of the stiffening element 60 may be arranged to be absent of back sheet to improve breathability of the article.

Main features of the stiffening element 60, besides the flatness, are inter alia: i) that it extends in the longitudinal direction of the article 100 over the crotch portion 3 and at least some way in over the front portion 2; ii) that it has a width H at the transition 27 between the crotch and front portions 3, 2 that is within the range of 15-45 mm; iii) that it has a length G in the crotch portion 3 within the range of 70-120 mm; iv) that the side edges of the stiffening element 60, in the direction from the crotch area in over the front portion 2, form an acute angle α (i.e. <90°, preferably 35-55°) with a line in the longitudinal direction of the article 100; and v) that it also extends some way in over the rear portion 4 and has a wedge-shaped cutout 66 extending from a rear end edge of the stiffening element 60 in a direction towards the crotch portion 3, as a result of which the product is, during use, imparted a fold along the longitudinal direction of the article 100 in the cutout 66. The fold extends into the cleft between the buttocks of the wearer during use of the article 100. These features all contribute to the fit of the article to the wearer during use. One or several of these features may be used to enhance the fit of the article.

FIG. 4 shows, in a schematic view, an absorbent article 101 with a second example of a suitable shape of a stiffening element 70. In this case, the stiffening element 70 includes three parts; one front element located substantially in the front portion 2 and two rear, elongated elements that extends in parallel in the longitudinal direction in the rear portion 4 and partly the crotch portion 3 of the article 101. In the example shown, the front and rear elements are all rectangular in order to simplify production and avoid wastage. Of course, these elements may be more or less rounded off such as to increase comfort (avoid chafe). In particular, the rear corners of the front element may need to be rounded off, depending on the exact positioning and the stiffness of the front stiffening element 70. The front element provides a three-dimensional bowl-like shape in an area in the front portion 2. The rear elements provide a fold along the longitudinal direction of the article 101 in similarity to the rear part of the stiffening element shown in FIG. 3. In the example shown in FIG. 4, an absence of stiffening elements in the transition zone 27 between the front and crotch portions 2, 3 provides for a suitable width of the article 101 in this position.

As shown in FIGS. 3 and 4, the absorption article 100,101 may be provided with fastening wings 30 provided with adhesives (not shown in the figures) for enhanced attachment of the article to the undergarments of the wearer. Such wings are known.

FIG. 5 shows, in a schematic view, an absorbent article 102 with a third example of a suitable shape of a stiffening element 80. In this case, the stiffening element 80 has the shape of a spoon with a three-dimensional bowl-shaped part located in the front portion 2, and a more narrow part extending over the crotch portion 3, where a hump is formed, and somewhat into the rear portion 4 as to produce a rearward leakage protection as described above.

The invention is not limited by the embodiments described above but can be modified in various ways within the scope of the claims. For instance, the stiffening element, irrespective of whether it includes hook material, friction adhesive material or a combination thereof, does not necessarily have to be made entirely of this or these materials. The stiffening element may e.g. include layers of different materials that together build up the total stiffness. What is important is that the stiffness is sufficient for giving the absorbent article a suitable, predetermined shape during use and that the outer side of the stiffening element exhibits mechanical fastening properties.

The stiffening element may be articulated for increasing longitudinal flexibility of the article. "Hinges" for this purpose can be arranged in the form of longitudinally distributed slits or hook-free regions if the piece of material making up the stiffening element includes a hook material.

Foam is an example of a material useful for forming the stiffening element.

The stiffening element can be secured to the lower side of the absorption member by means of e.g. adhesives and/or treatment by ultrasonic waves, heat or laser.

The absorbent article may or may not include the secondary, lower absorption member 20 shown in FIG. 2. The upper and lower absorption members 5',20 may be packaged or sold separately and be assembled by a user prior to use. The lower absorption member 20 can be provided with markers for proper positioning of the upper absorption member 5. For instance, the upper side 25 of the lower absorption member 20 can be provided with a marker in the form of a line corresponding to an outer edge of the upper absorption member 5'.

What is claimed is:

1. An absorbent article having a longitudinal direction, a transverse direction, a front portion, a rear portion, and a crotch portion located between the front portion and the rear portion, said article comprising:
    an absorption member having an upper side intended to face a wearer during use of the article and a lower side intended to face away from the wearer during use of the article, and
    a stiffening element that, at least during use of the article, provides the article with a predetermined shape that enhances the fit of the article to the wearer's body,
    wherein the stiffening element is secured to the lower side of the absorption member such that an outer side of the stiffening element faces away from the absorption member, and the stiffening element comprises a material exhibiting mechanical fastening properties at least on a part of the outer side of the stiffening element,
    wherein the material exhibiting mechanical fastening properties also contributes to the stiffness of the stiffening element, and the material comprises a hook material having hooks protruding from the outer side of the stiffening element for fastening to a textile material,
    wherein the hook material comprises a hook carrier layer to which layer the hooks are secured, and the hook material contributes to the stiffness and constitutes the stiffening element,
    wherein the absorption member includes an absorbent body for absorbing body fluids and a liquid-permeable top sheet arranged at the upper side of the absorption member, and a liquid-impermeable hack sheet arranged at the lower side of the absorption member,
    wherein the absorbent body is arranged between the top sheet and the back sheet, and
    wherein the stiffening element that is arranged on the lower side of the absorption member includes a wedge-shaped cutout extending from a rear end edge in a direction towards the crotch portion.

2. The absorbent article according to claim 1, wherein the material exhibiting mechanical fastening properties further comprises a friction adhesive material.

3. The absorbent article according to claim 2, wherein the friction adhesive material also constitutes the stiffening element.

4. The absorbent article according to claim 1, wherein the stiffening element exhibits a stiffness that is higher than a part of the absorbent article that surrounds the stiffening element.

5. The absorbent article according to claim 1, wherein the stiffening element is stiffer than the absorption member.

6. The absorbent article according to claim 1, wherein the stiffening element forms at least a part of the back sheet.

7. The absorbent article according to claim 1, wherein the article further comprises a secondary absorption member that is detachably attachable to the stiffening element such as to be positioned below the absorption member to which the stiffening element is secured.

8. The absorbent article according to claim 7 wherein the secondary absorption member extends further in the transversal direction than the absorption member.

9. The absorbent article according to claim 8, wherein the secondary absorption member also extends further in the longitudinal direction than the absorption member.

10. The absorbent article according to claim 1, wherein the stiffening element that is arranged on the lower side of the absorption member includes a circular portion arranged in the front portion.

* * * * *